United States Patent [19]
Nicholson et al.

[11] Patent Number: 5,162,375
[45] Date of Patent: * Nov. 10, 1992

[54] TREATMENT OF NEURONAL DEGENERATION WITH 5HT1$_A$ AGONISTS

[75] Inventors: Charles D. Nicholson, Glasgow, Scotland; Johannes Jukna, Gronau, Fed. Rep. of Germany

[73] Assignee: Beecham Group p.l.c., England

[*] Notice: The portion of the term of this patent subsequent to Sep. 17, 2008 has been disclaimed.

[21] Appl. No.: 662,784

[22] Filed: Feb. 28, 1991

Related U.S. Application Data

[62] Division of Ser. No. 348,859, May 8, 1989, Pat. No. 5,049,588.

[30] Foreign Application Priority Data

May 6, 1988 [GB] United Kingdom ............... 88107487

[51] Int. Cl.$^5$ .......................................... A61K 31/135
[52] U.S. Cl. ..................................... 514/646; 514/657
[58] Field of Search ................................ 514/646, 657

[56] References Cited

FOREIGN PATENT DOCUMENTS 41488 12/1981 European Pat. Off. .
171728 1/1986 European Pat. Off. .
3719924 6/1988 Fed. Rep. of Germany .

OTHER PUBLICATIONS

J. Neurochemistry, 46(3), pp. 993–996 (1986).
J. Cardiovascular Pharmacology, 9(3), pp. 328–347 (1987).
Eur. J. Pharmacol, 183(5), pp. 1953–1954 (1990).
Villacara, A. et al, J Neurochem 53(2):595–601 1989.

Primary Examiner—Frederick E. Waddell
Assistant Examiner—Diane Gardner
Attorney, Agent, or Firm—Roseman & Colin

[57] ABSTRACT

A method for the treatment and/or prophylaxis of disorders associated with neuronal degeneration resulting from ischaemic events, in mammals, such as humans, which comprises administering to the mammal in need of such treatment an effective amount of a 5-HT1$_A$ agonist.

9 Claims, No Drawings

TREATMENT OF NEURONAL DEGENERATION WITH 5HT$_{1A}$ AGONISTS

CROSS-REFERENCE

This is a division of Ser. No. 348,859 filed May 8, 1989 which issues as U.S. Pat. No. 5,049,588 on Sep. 17, 1991.

The present invention relates to a method for the treatment and/or prophylaxis of disorders associated with neuronal degeneration resulting from ischaemic events.

EP-0041488 discloses 8-hydroxy-2-(di-n-propylamino) tetralin and a process by which it can be prepared. This compound, is described in the patent as a 5-HT-receptor agonist of potential use in the therapy of CNS disorders, in particular depression, and of sexual disturbances.

It has now been discovered that the compound has neuroprotectant activity. 8-Hydroxy-2-(di-n-propylamino) tetralin is therefore useful in the treatment and/or prophylaxis of disorders associated with neuronal degeneration resulting from ischaemic events, including cerebral ischaemia after cardiac arrest, stroke and multi-infarct dementia and also after cerebral ischaemic events such as those resulting from surgery and/or during childbirth.

Accordingly, the present invention provides a method for the treatment and/or prophylaxis of disorders associated with neuronal degeneration resulting from ischaemic events in mammals, such as humans, which comprises administering to the mammal in need of such treatment an effective, non toxic amount of a 5-HT$_{1A}$ agonist.

Suitably, the 5-HT$_{1A}$ agonist is a full 5-HT$_{1A}$ agonist.

Preferably, the 5-HT$_{1A}$ agonist is 8-hydroxy-2-(di-n-propylamino)tetralin, or a pharmaceutically acceptable salt thereof.

Suitable ischaemic events include cerebral ischaemia after cardiac arrest, stroke and multi-infarct dementia.

Further suitable ischaemic events include cerebral ischaemia which may result from surgery.

Also to be mentioned is the cerebral ischaemia which may occur in newborns during birth.

The administration to the mammal may be by way of oral, sub-lingual or parenteral administration as appropriate.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 50 mg such as 2, 5, 10, 20, 30, 40 or 50 mg of the active compound. Unit doses will normally be administered once or more than once per day, for example 2, 3, 4, 5 or 6 times a day, more usually 2 to 4 times a day, such that the total daily dose is normally in the range, for a 70 kg adult of 1 to 1000 mg, for example 50 to 250 mg, that is in the range of approximately 0.01 to 15 mg/kg/day, more usually 1 to 4 mg/kg/day, for example 0.7 to 2 mg/kg/day.

It is greatly preferred that the active compound is administered in the form of a unit-dose composition, such as a unit dose oral, sub-lingual or parenteral composition.

Such compositions are prepared by admixture and are suitably adapted for oral, sub-lingual or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral and sub-lingual administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active compound throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing an active compound of the present invention and a sterile vehicle. The active compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

As used herein the terms "pharmaceutical composition" and "pharmaceutically acceptable" embrace compositions and ingredients for both human and veterinary use.

When used herein the term '5HT$_{1A}$ agonist' relates to a compound which binds to a 5HT$_{1A}$ receptor and ellicits a biological response.

When used herein the term 'full 5HT$_{1A}$ agonist' relates to a compound being substantially free from 5HT$_{1A}$ antagonist activity.

When used herein the term '5HT$_{1A}$ antagonist activity' relates to a compound which binds to a 5HT$_{1A}$ receptor and acts to block the biological response.

Examples of pharmaceutically acceptable salts of the compound include the hydrobromide.

The present invention also provides a 5-HT$_{1A}$ agonist for use in the treatment and/or prophylaxis of disorders associated with neuronal degeneration resulting from ischaemic events in mammals, such as humans.

Such treatment may be carried out as hereinbefore described.

The present invention further provides a pharmaceutical composition for use in the treatment and/or prophylaxis of disorders associated with neuronal degeneration resulting from ischaemic events in mammals, such as humans, which comprises an effective amount of a 5-HT$_{1A}$ agonist and a pharmaceutically acceptable carrier.

Such composition may be prepared in a manner as described hereinbefore.

In a further aspect the invention provides the use of a 5-HT$_{1A}$ agonist for the manufacture of a medicament for the treatment and/or prophylaxis of disorders associated with neuronal degeneration resulting from ischaemic events in mammals, such as humans.

Such composition (medicament) may be prepared in the manner as hereinbefore described.

The following pharmacological data illustrate the neuroprotectant activity of the active compound in tests which are indicative of compounds of potential use in the treatment of the invention. cl Pharmacological Data Delayed neuronal death in gerbils after transient forebrain ischaemia Method A Ischaemia-induced nerve cell degeneration was produced in adult male gerbils by occlusion of both common carotid arteries for 3 minutes under halothane/nitrous oxide anaesthesia. Brains were removed 1 week later and 7μM thick coronal slices were examined light microscopically for neuronal degeneration.

3 groups of animals were used
1. sham ligated controls
2. solvent-treated ligated controls
3. compound-treated ligated animals The test compound 8-hydroxy-2-(di-n-propylamino) tetralin (HBr salt) was administered intraperitoneally as an aqueous solution either 1 hour before or 1 hour after the start of the ligation period.

Method B

In an alternative procedure, the animals were placed upon a warming blanket during the carotid artery occlusion, to avoid a drop in body temperature. The brains were then removed 2 weeks later and 12μm thick coronal slices were examined light microscopically for neuronal degeneration.

The remaining procedure was identical to that described in Method A.

Results means±SEM (n) of a histopathological score which reflects the degree of neuronal damage in the hippocampal CA1 field:
0=no damaged neurons,
1=mild necrosis,
2=moderate necrosis,
3=severe necrosis,
4=complete necrosis.

In addition, the percentage of healthy animals is specified.

| Method A | Sham ligated controls | Solvent treated ligated controls | Ligated animals treated with active compound 10 mg/kg test compound i.p. | |
|---|---|---|---|---|
| | | | 1 hr pre-ligation | 1 h post-ligation |
| Histopathological score (artificial units) | 0* (4) | 2.1 ± 0.2 (55) | 0* ± 0 (6) | 0.7* ± 0.2 (18) |
| Healthy animals (%) | 100* | 25 | 100* | 56* |

| Method B | Sham ligated controls | Solvent treated ligated controls | ligated animals treated with active compound | |
|---|---|---|---|---|
| | | | 1 mg/kg 1 hr pre-ligation | 10 mg/kg 1 h post-ligation |
| Histopathological score (artificial units) | 0* (4) | 3.4 ± 0.1 (48) | 1.3* ± 0.5 (7) | 1.8* ± 0.6 (8) |
| Healthy animals (%) | 100* | 2 | 14 | 13 |

*Significantly (p < 0.05) different from solvent treated ligated controls.

I claim:

1. A method for the treatment and/or prophylaxis of disorders associated with neuronal degeneration resulting from ischaemic events in mammals, which comprises administering to the mammal in need of such treatment an effective, non-toxic amount of a 5-HT$_{1A}$ agonist.

2. A method according to claim 1, wherein the 5-HT$_{1A}$ agonist is a full 5-HT$_{1A}$ agonist.

3. A method according to claim 1, wherein the ischaemic event includes cerebral ischaemia after cardiac arrest, stroke and multi-infarct dementia.

4. A method according to claim 1, wherein the ischaemic event includes cerebral ischaemia resulting from surgery or that which may occur in newborns during birth.

5. A method according to claim 1, wherein the agonist is administered as a unit dose composition.

6. A method according to claim 5, wherein the unit dose comprises from 1 to 500 mg of the agonist.

7. A method according to claim 5, wherein the unit dose comprises from 2 to 50 mg of the agonist.

8. A method according to claim 1, wherein the agonist is administered by parenteral administration.

9. A method according to claim 1, wherein the agonist is administered by oral administration.

* * * * *